United States Patent
Masui et al.

(10) Patent No.: US 7,343,984 B2
(45) Date of Patent: Mar. 18, 2008

(54) CORE SAMPLE COLLECTOR EQUIPPED WITH STERILIZING AGENT-APPLYING MECHANISM AND METHOD OF TAKING CORE SAMPLE

(75) Inventors: Noriaki Masui, Kanagawa (JP); Shigeru Deguchi, Kanagawa (JP); Kaoru Tsujii, Kanagawa (JP); Hiroshi Kitazato, Kanagawa (JP)

(73) Assignee: Independent Administrative Institution, Japan Agency for Marine-Earth Science and Technology, Yokosuka-shi (JP)

( * ) Notice: Subject to any disclaimer, the term of this patent is extended or adjusted under 35 U.S.C. 154(b) by 820 days.

(21) Appl. No.: 10/771,983

(22) Filed: Feb. 3, 2004

(65) Prior Publication Data

US 2005/0106751 A1    May 19, 2005

(30) Foreign Application Priority Data

Nov. 14, 2003   (JP) .............................. 2003-384681

(51) Int. Cl.
*E21B 49/00* (2006.01)

(52) U.S. Cl. .......................................... 175/58; 175/20

(58) Field of Classification Search ................ 175/20, 175/58, 226, 233, 249; 73/864.44, 864.45, 73/863.21
See application file for complete search history.

(56) References Cited

U.S. PATENT DOCUMENTS

| | | | | |
|---|---|---|---|---|
| 2,862,691 A * | 12/1958 | Cochran | ..................... | 175/226 |
| 2,880,969 A * | 4/1959 | Williams | ..................... | 175/226 |
| 6,695,076 B2 * | 2/2004 | Masui et al. | ................... | 175/58 |
| 7,013,993 B2 * | 3/2006 | Masui et al. | ................... | 175/58 |
| 7,124,841 B2 * | 10/2006 | Wada et al. | ................. | 175/226 |
| 2002/0139583 A1 * | 10/2002 | Masui et al. | ................... | 175/58 |
| 2004/0026127 A1 * | 2/2004 | Masui et al. | ................... | 175/58 |
| 2004/0256151 A1 * | 12/2004 | Wada et al. | ..................... | 175/20 |
| 2005/0106751 A1 * | 5/2005 | Masui et al. | ................. | 436/174 |
| 2005/0183886 A1 * | 8/2005 | Masui et al. | ................... | 175/20 |

\* cited by examiner

*Primary Examiner*—Jennifer H. Gay
*Assistant Examiner*—Daniel P Stephenson
(74) *Attorney, Agent, or Firm*—Frishauf, Holtz, Goodman & Chick, P.C.

(57) ABSTRACT

A core sample collector includes a cylinder and a piston, wherein the piston includes a piston body, upper piston rings and lower piston rings, and a sterilizing agent is held in a space defined between the piston, the cylinder, the upper piston ring and the lower piston ring. The sterilizing agent may be an antimicrobial polymeric gel. A core sample is collected by contacting the cylinder against a surface from which the core sample is to be taken, and causing relative movement between the cylinder and the piston such that: (i) the sterilizing agent is applied to the inner peripheral wall surface of the cylinder, (ii) the upper and lower piston rings scrape the sterilizing agent from the inner peripheral wall, and (iii) a core is received in the cylinder.

18 Claims, 6 Drawing Sheets

CORE SAMPLE COLLECTOR EQUIPPED WITH STERILIZING AGENT-APPLYING MECHANISM AND METHOD OF TAKING CORE SAMPLE

BACKGROUND OF THE INVENTION

1. Field of the Invention

The present invention relates to a core sample collector equipped with a sterilizing agent-applying mechanism, which is used in taking, for example, a core sample for researches on subsurface microorganisms, and a method of taking a core sample.

2. Description of the Background Art

It is necessary to take a core sample for researches on subsurface microorganisms, and, for example, a piston corer has heretofore been often used as a core sample collector for taking such a core sample.

Such a piston corer is equipped with a tube-shaped cylinder functioning as the so-called sampling tube extending in, for example, vertical directions, and a column shaped piston arranged freely movably within this cylinder, and collects a core sample by receiving it in the cylinder.

Since it is difficult to make an inner peripheral wall surface of the cylinder a biologically clean state that nonindigeneous microorganisms are absent upon taking the core sample using such a piston corer, the nonindigeneous-microorganisms unavoidably adhere to the core sample due to the contact of the core sample with the inner peripheral wall surface of the cylinder upon taking the core sample. As a result, the core sample taken has a great possibility that the state of the sample present in the crust as it is may be lost and become unsuitable for use in researches on subsurface microorganisms.

However, no effective method for preventing such contamination with the nonindigeneous microorganisms has heretofore been known.

SUMMARY OF THE INVENTION

The present invention has been made on the basis of the foregoing circumstances and has as its object the provision of a core sample collector able to take a core sample which has no possibility of microbial contamination from the outside and suitable for use in researches on subsurface microorganisms.

Another-object of the present invention is to provide a method of taking a core sample using the core sample collector described above.

According to the present invention, there is thus provided a core sample collector comprising a cylinder extending in vertical directions and a piston arranged movably within this cylinder, wherein the piston is equipped with a sterilizing agent-applying mechanism for applying a cleaning or sterilizing agent to an inner peripheral wall surface of the cylinder and a sterilizing agent-scraping member for scraping the sterilizing agent applied by the sterilizing agent-applying mechanism as it moves within the cylinder.

In the present invention, it may be preferred that the piston be composed of a piston body, upper piston ring and lower piston ring making up the sterilizing agent-scraping member, the upper piston ring and lower piston ring be arranged so as to project outward in a radial direction from an outer peripheral surface of the piston body and slidably come into contact with the inner peripheral wall surface of the cylinder, and the sterilizing agent-applying mechanism be made up by holding the sterilizing agent within a space formed by partitioning a vacant space between the piston and the cylinder with the upper piston ring and the lower piston ring.

The sterilizing agent-applying mechanism may also preferably be made up by arranging a sterilizing agent carrier within the space formed by partitioning the vacant space between the piston and the cylinder with the upper piston ring and the lower piston ring and causing the sterilizing agent to be carried and held on the sterilizing agent carrier.

The sterilizing agent may preferably be an antimicrobial or bactericidal plastic polymeric substance.

According to the present invention, there is also provided a method of taking a core sample, comprising using the core sample collector described above to collect the core sample.

According to the core sample collector of the present invention, a sterilizing agent is applied to a region in the inner peripheral wall surface of the cylinder that is a sampling tube, with which a core sample comes into contact, right before the core sample comes into contact, whereby a sterilized state or a biologically clean state is created, and the sterilizing agent applied to the inner peripheral wall surface is thereafter scraped by the scraping member and surely removed. Therefore, a core sample free of both contamination with nonindigeneous microorganisms from the outside and disorder of a biological state caused by the sterilizing agent and suitable for use in researches on microorganisms can be collected with certainty.

BRIEF DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE PREFERRED EMBODIMENTS

The present invention will hereinafter be described in detail with reference to the accompanying drawings.

Figure 1:
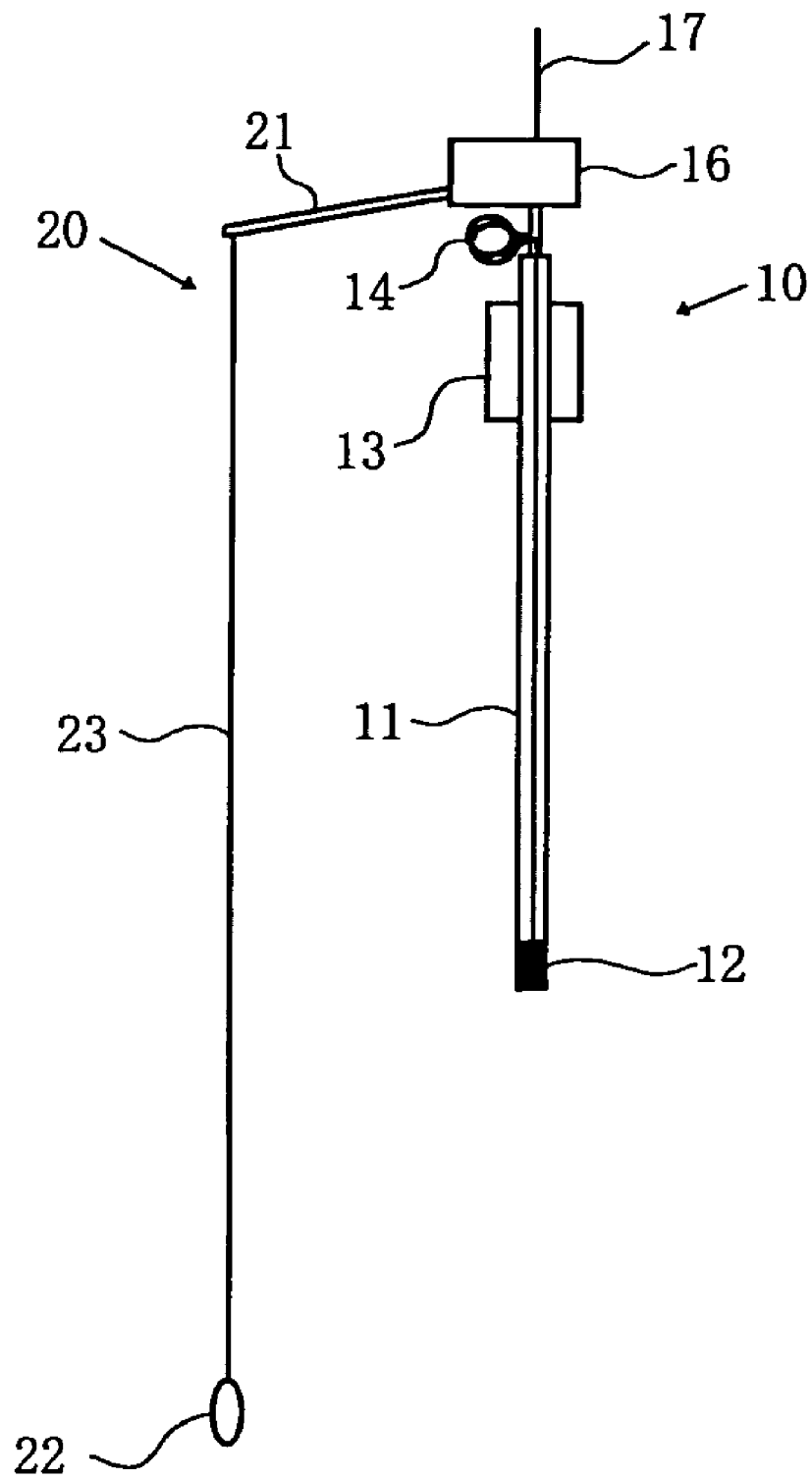
FIG. 1 illustrates an exemplary piston corer equipped with a sterilizing agent-applying mechanism.
Figure 2:
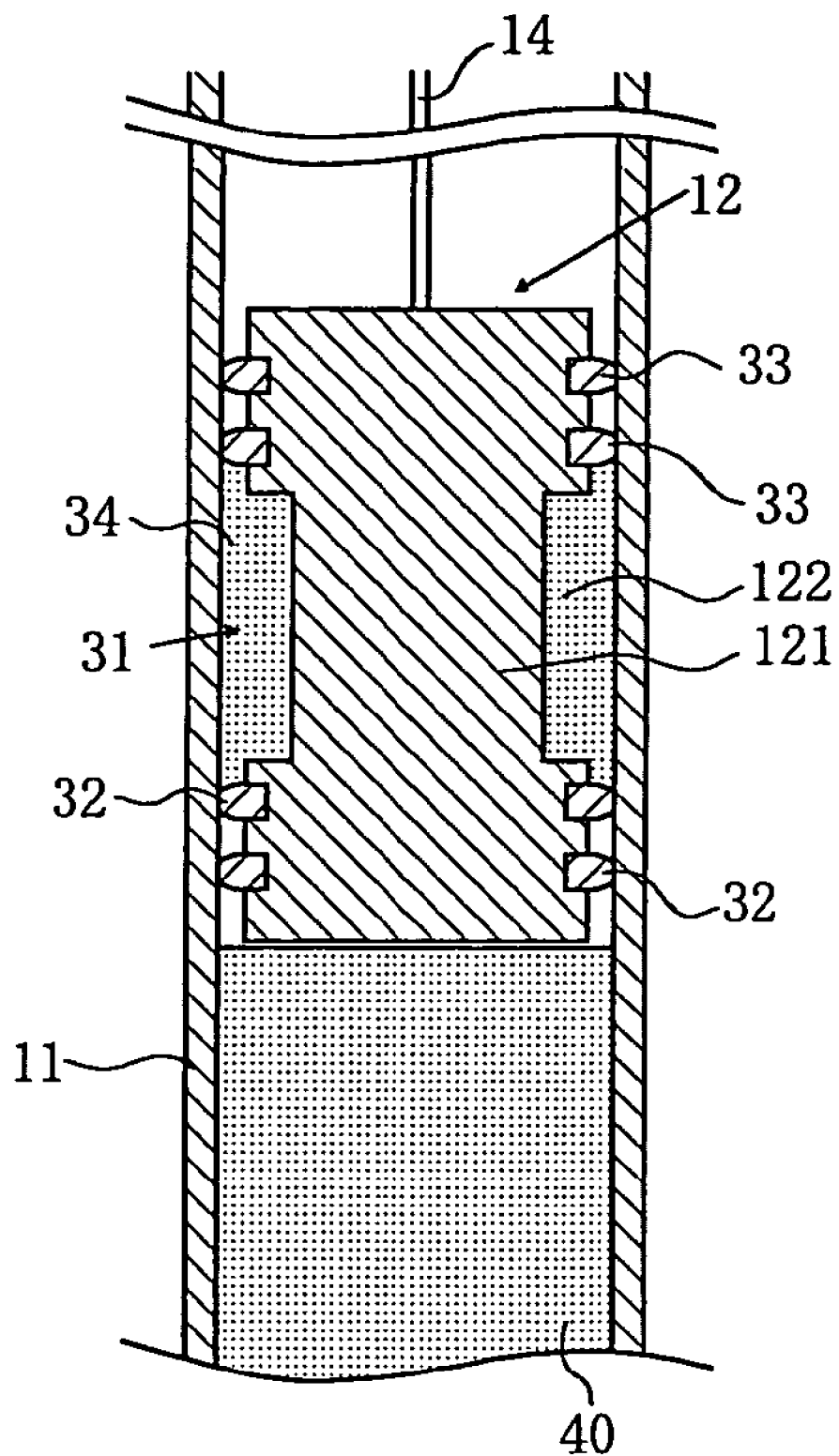
FIG. 2 is an enlarged sectional view illustrating the construction of an exemplary piston in the piston corer shown in FIG. 1, with the section taken along the axis of a cylinder.

FIG. 1 illustrates an exemplary piston corer equipped with a sterilizing agent-applying mechanism, which is a core sample collector according to the present invention, and FIG. 2 is an enlarged sectional view illustrating the construction of an exemplary piston in the piston corer shown in FIG. 1, with the section taken along the axis of a cylinder.

In FIG. 1, a piston corer 10 that is a core sample collector is constructed by a support part 16 supported by a main wire 17 vertically extending, a cylinder 11 detachably installed on the support part 16 and extending in vertical directions, a column shaped piston 12 suspended and supported within the cylinder 11 by a supporting member 14 composed of a wire extending from the support part 16 and air-tightly movable in an internal space of the cylinder 11, and a trigger mechanism 20 provided at the support part 16.

Reference numerals 13 and 40 indicate a main sinker integrally provided on an upper part of the cylinder 11 and a core sample received in the cylinder 11, respectively.

The cylinder 11 functions as the so-called sampling tube that is hollow and cylindrical, and no particular limitation is imposed on a material thereof. As examples thereof, may be mentioned metals such as stainless steel and resins such as polypropylene and reinforced plastics filled with various reinforcing materials.

In the cylinder 11, the inner diameter and length thereof may be suitably selected according to research objects or the like of the core sample 40. Specifically, for example, that having an inner diameter of 5 to 15 cm, particularly 8 cm and a length of 1 to 20 m, particularly 5 to 10 m may be preferably used.

The piston 12 is composed of a piston body 121, 2 upper piston rings 33 arranged substantially in parallel with each other on an upper portion of an outer peripheral surface of the piston body 121, 2 ring-like lower piston rings 32 arranged substantially in parallel with each other which making up a cleaning agent-scraping member at a lower portion of the outer peripheral surface, and a sterilizing agent-applying mechanism 31. The upper piston rings 33 and lower piston rings 32 are arranged substantially in parallel with each other and with a space.

The piston body 121 is a column shaped body having an outer diameter smaller than an inner diameter of the cylinder 11, and a recessed portion having an outer diameter smaller than the piston body 121 is formed over the whole periphery thereof in a region between the upper piston ring 33 and the lower piston ring 32, thereby forming a sterilizing agent reservoir 122 making up the sterilizing agent-applying mechanism 31, which will be described subsequently.

In this embodiment, a sterilizing agent carrier may be arranged in the sterilizing agent reservoir 122.

The piston body 121 is suspended and supported movably within the cylinder 11 by being connected to the supporting member 14 at an upper end thereof.

The outer diameter of the piston body 121 is preferably such a size that a difference with the inner diameter of the cylinder 11 is 2 to 15 mm, particularly 2 to 10 mm, more particularly 5 to 10 mm.

No particular limitation is imposed on a material for forming the piston body 121 so far as it has specific strength. As examples thereof, may be mentioned stainless steel, aluminum alloys, reinforced plastics and fluororesins.

The sterilizing agent carrier is preferably suitably selected according to a state of the sterilizing agent 34 used. For example, when the sterilizing agent is a plastic polymeric substance, which will be described subsequently, for example, a netted carrier may be used. When the sterilizing agent is liquid, for example, porous substances such as sponge and synthesized sponge, aggregates of vegetable fibers such as pulp and cotton, aggregates of animal fibers such as silk, organic chemical fibers composed of polyethylene or the like, inorganic chemical fibers such as glass wool, etc. may be suitably used. Specifically, KIM TOWEL (trademark, product of CRECIA Corporation), cotton towel or the like may preferably be used.

By using this carrier, the sterilizing agent is impregnated into the sterilizing agent carrier even when the sterilizing agent is liquid, whereby it is surely retained in the sterilizing agent reservoir 122 in a proper mode.

The lower piston rings 32 are composed of, for example, a resinous O-ring that is an elastic material and arranged so as to project outward in a radial direction from an outer peripheral surface of the piston body 121 and air-tightly slidably come into contact at the peripheral edge portion thereof with the inner peripheral wall surface of the cylinder 11 over the whole periphery thereof.

By arranging these 2 lower piston rings 32 double, the sterilizing agent 34 can be surely scraped and removed from the inner peripheral wall surface of the cylinder 11.

The upper piston rings 33 are composed of, for example, a resinous O-ring that is an elastic material, particularly preferably formed of the same material as that used in the lower piston rings 32 and arranged so as to project outward in a radial direction from an outer peripheral surface of the piston body 121 and air-tightly slidably come into contact at the peripheral edge portion thereof with the inner peripheral wall surface of the cylinder 11 over the whole periphery thereof.

The projected height of each of the lower piston rings 32 and upper piston rings 33 is preferably, for example, 2.5 to 7.5 mm, particularly 5 mm.

The length of the wire that is the supporting member 14 is defined to a specific length in advance. In other words, the sum of the overall length of the supporting member 14 and the length of the piston 12 is set to a length equal to a distance from the lowest portion of the support part 16 to a sea floor and is a length equal to said distance at the time the trigger mechanism 20, which will be described subsequently, is operated, and the cylinder 11 is detached from the support part 16.

No particular limitation is imposed on the supporting member 14. Even when the supporting member 14 is composed of a wire, no particular limitation is also imposed on the material and diameter thereof, and that satisfying strength required from the viewpoint of practical use according to the weight of the cylinder 11, the weight of the main sinker 13 and the like may be suitably selected.

The sterilizing agent-applying mechanism 31 is made up by filling and holding the sterilizing agent 34 into and within the sterilizing agent reservoir 122 substantially closed tightly and which is formed by partitioning a vacant space between an outer peripheral surface of the piston body 121 and an inner peripheral wall surface of the cylinder 11 with the upper piston ring 33 and the lower piston ring 32, which are arranged closely to each other at a central portion of the piston body 121.

The trigger mechanism 20 is constructed by a trigger rod 21 provided movably in vertical directions at the support part 16 and a lead sinker 22 suspended and supported by a wire 23 at the tip end of the trigger rod 21. In this embodiment, the lead sinker 22 is in a state suspended below the lowest end of the cylinder 11 in a state installed on the support part 16. In FIG. 1, the trigger rod 21 is in a state controlled at a lower position by the leading sinker 22.

The method of taking a core sample making use of such a piston corer as described above will now be described in detail with reference to FIGS. 3 to 6.

Figure 3:
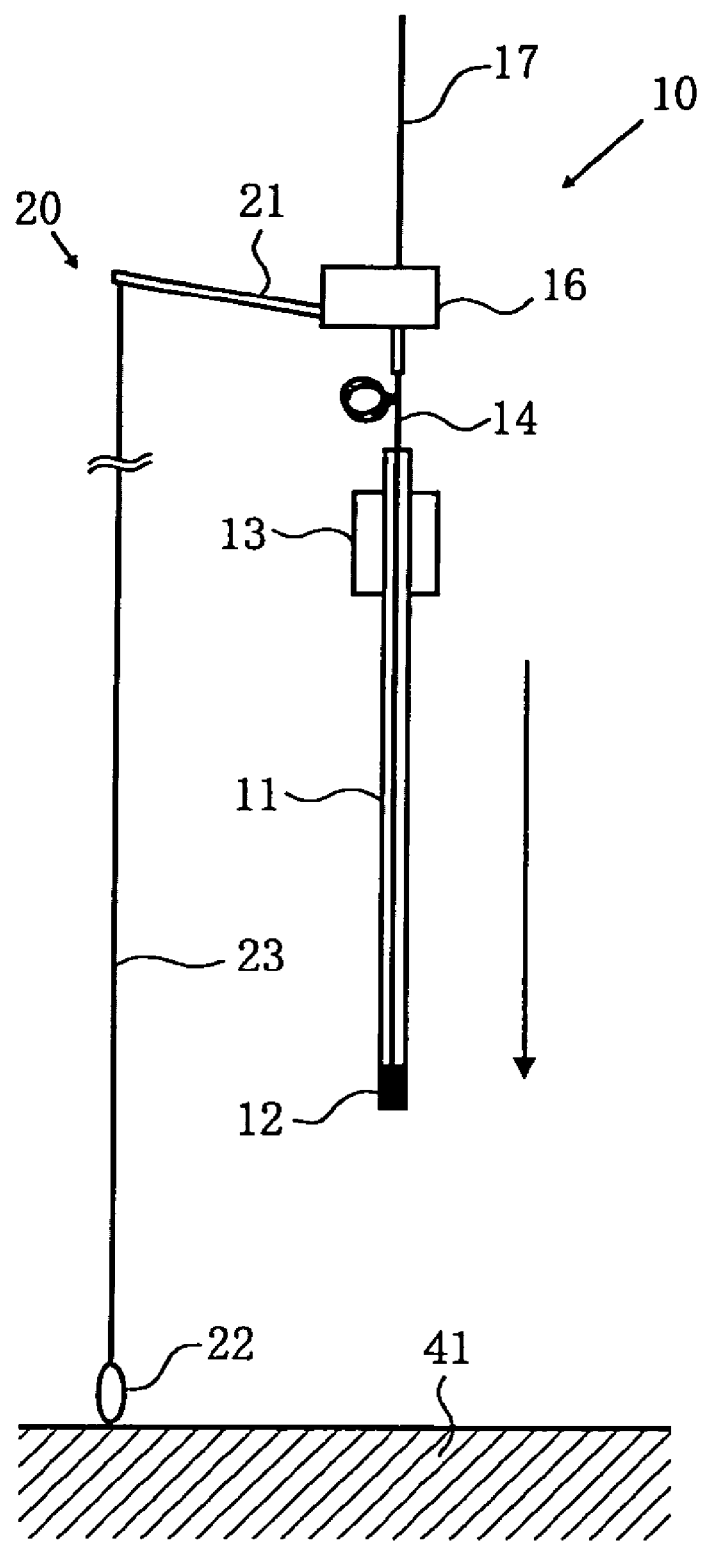
FIG. 3 illustrates, partly in cross section, a method of taking a core sample making use of the piston corer.
Figure 4:
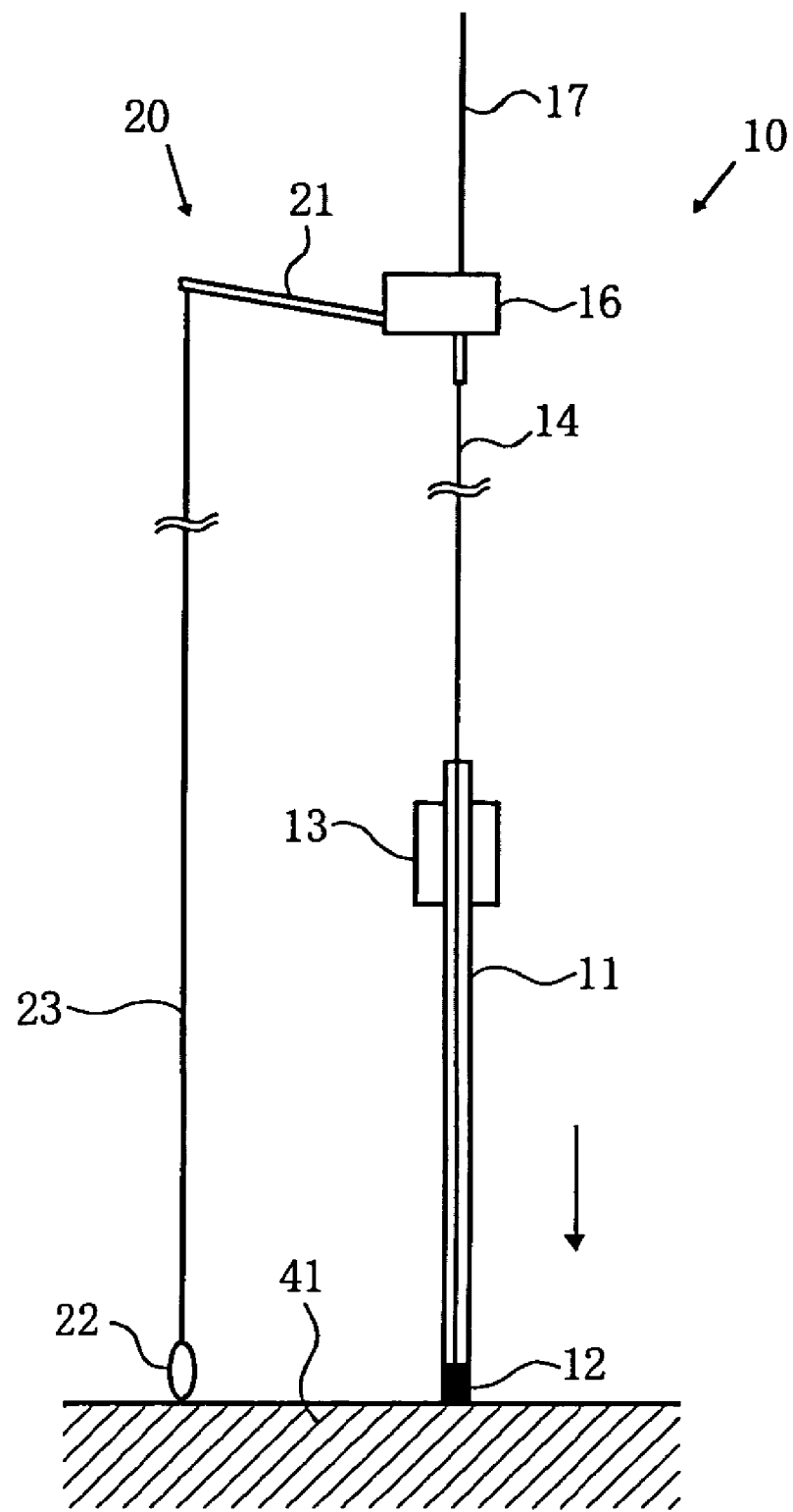
FIG. 4 illustrates, partly in cross section, the method of taking a core sample making use of the piston corer.

When the piston corer 10 is first lowered into the sea and suspended to a position of a specific distance from the sea bottom as illustrated in FIGS. 3 and 4, the lead sinker 22 comes into contact with the sea floor, and the trigger rod 21 is moved at an upper position interlocking with this, whereby the trigger mechanism 20 is operated, and so the cylinder 11 is detached from the support part 16.

The cylinder 11 detached from the support part 16 automatically falls together with the piston 12 by virtue of gravity and the like. However, the lowest end of the piston 12 is prevented from sinking below the sea floor because the supporting member 14 supporting the piston 12 has the specific length as described above, and is forcedly stopped to a position substantially equal to the sea floor.

On the other hand, the cylinder 11 continues falling by its own gravity and the force of inertia of falling to penetrate into a sediment layer 41, along with relative movement of the piston 12 toward an upper portion of the cylinder 11. As a result, a state of negative pressure is created in a space below the piston 12 in the cylinder 11, and a core sample 40 is sucked and received into the interior of the cylinder 11 from the tip thereof by the action of the negative pressure.

With the relative movement of the piston 12 to the cylinder 11 toward the upper portion, a sterilizing agent 34 is applied to an inner peripheral wall surface of the cylinder 11 by the sterilizing agent-applying mechanism 31, and immediately after this, the sterilizing agent 34 applied is scraped and removed by the lower piston rings 32 located at lower part of the sterilizing agent-applying mechanism 31.

Figure 5:
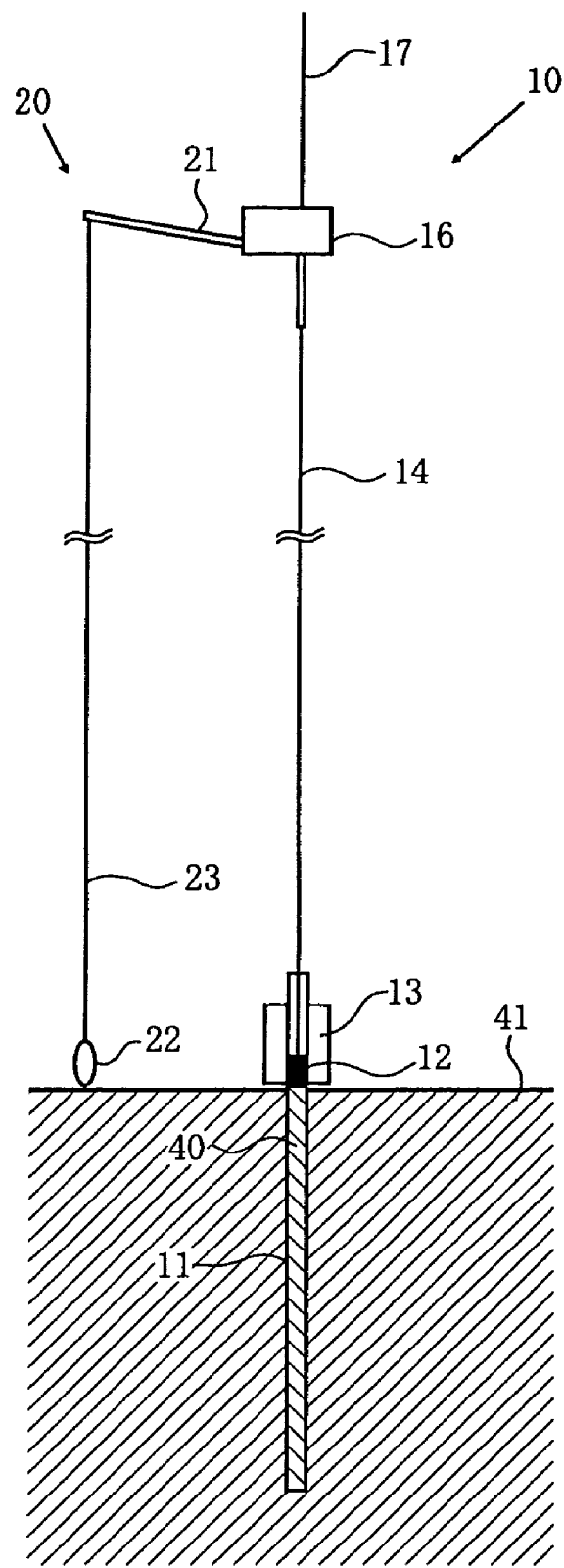
FIG. 5 illustrates, partly in cross section, the method of taking a core sample making use of the piston corer.
Figure 6:
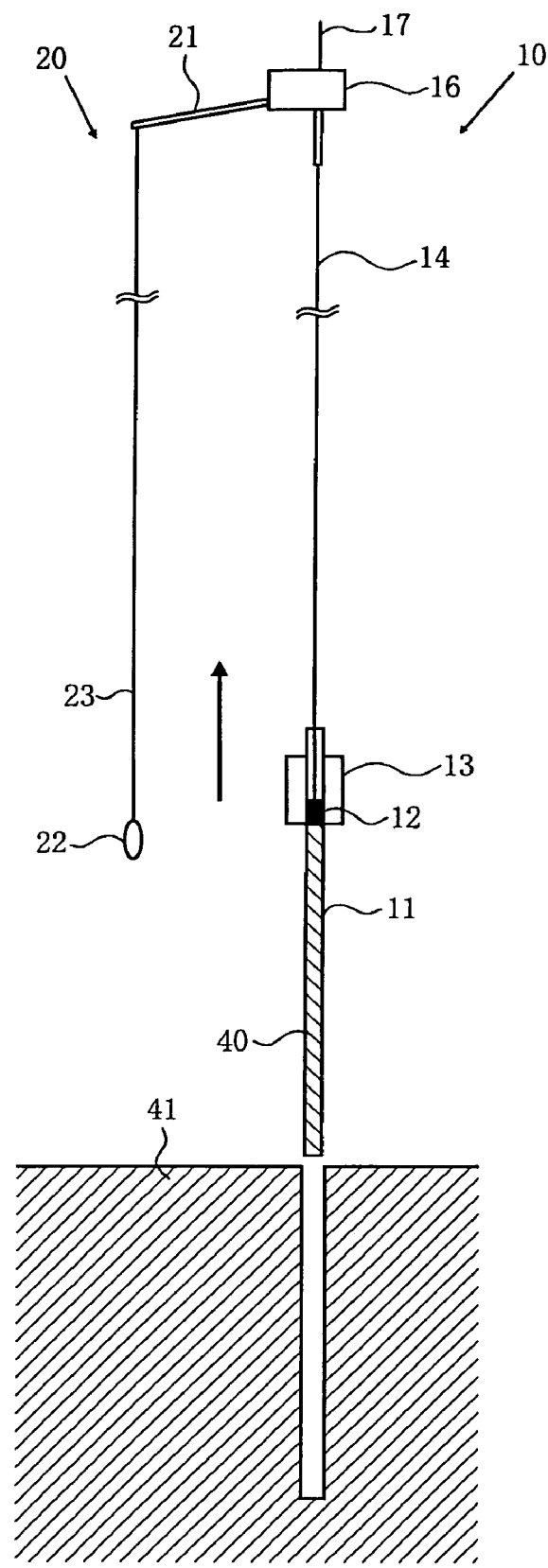
FIG. 6 illustrates, partly in cross section, the method of taking a core sample making use of the piston corer.

After the cylinder 11 is stopped as illustrated in FIG. 5, the whole piston corer 10 is lifted up as it is, whereby the cylinder 11 is pulled out of the sediment layer 41 through the supporting member 14. As illustrated in FIG. 6, the piston corer 10 is recovered above the sea surface as it is, thereby collecting the core sample 40.

In the method described above, no particular limitation is imposed on the sterilizing agent 34 used in the sterilizing agent-applying mechanism 31 of the piston 12 so far as it can create a sterilized or a biologically clean state on the inner peripheral wall surface of the cylinder 11, any of antimicrobial or bactericidal plastic polymeric substances, various antimicrobial agents or bactericides, etc. may be used.

As examples of the antimicrobial or bactericidal plastic polymeric substances, may be mentioned antimicrobial polymeric gel (hereinafter also referred to as "antimicrobial gel") that is a jam-like high-viscosity fluid obtained by polymerizing an antimicrobial monomer and composed of a polymer having antimicrobial activity by itself, and plastic polymeric substances composed of any of various polymers and any of various antimicrobial agents or bactericides dispersed in or impregnated into the polymer, such as gel (hereinafter also referred to as "inorganic antimicrobial gel") composed of any of various polymers and a substantially water-insoluble or hardly water-soluble inorganic antimicrobial agent (hereinafter also referred to as "specific inorganic antimicrobial agent").

As the antimicrobial agent or bactericide used as the sterilizing agent or used in the form carried on a polymer as described above, may be preferably used, for example, any of quaternary ammonium salts, phosphonium salts, cationic edible fiber antimicrobial agents such as chitosan, alcohol, ketone-aldehyde, phenol and iodine compound type bactericides, bactericides such as chlorine compounds, peroxides, heavy metal compounds and antibiotics, and those respectively containing these substances as an antimicrobial component or bactericidal component.

When these antimicrobial agents or bactericides are used as the sterilizing agent 34, such an antimicrobial agent or bactericide may be directly held in the sterilizing agent reservoir 122. However, it is particularly preferred that it be held in the sterilizing agent reservoir 122 in the form impregnated into the sterilizing agent carrier.

As the antimicrobial monomer for obtaining the polymer forming the antimicrobial gel, is used a compound having a polymerizable functional group having an unsaturated double bond and an antimicrobial atomic group in its molecule. As examples of such a compound, may be mentioned quaternary ammonium salt compounds having an unsaturated double bond and phosphonium salt compounds having an unsaturated double bond.

Specifically, one or more compounds selected from among an aromatic quaternary ammonium salt compound represented by the following general formula (1), an acryloyloxyalkyltrialkylammonium salt compound and a methacryloyloxyalkyltrialkylammonium salt compound represented by the following general formula (3), and an aromatic phosphonium salt compound represented by the following general formula (2) may preferably be used.

General formula (1):

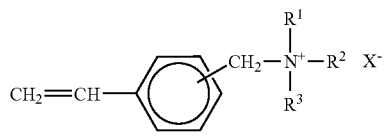

wherein $R^1$ means a linear or branched alkyl group having 1 to 18 carbon atoms, $R^2$ and $R^3$ are methyl groups, and $X^-$ denotes a halogen ion.

General formula (2):

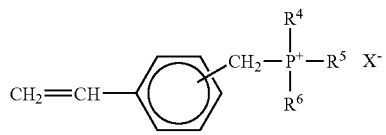

wherein $R^4$, $R^5$ and $R^6$ independently mean a linear or branched alkyl group having 1 to 18 carbon atoms, and $X^-$ denotes a halogen ion, with the proviso that $R^4$, $R^5$ and $R^6$ may be the same or different from one another.

General Formula (3):

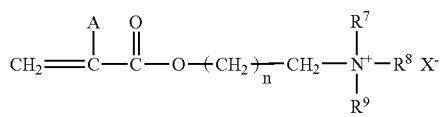

wherein $R^7$, $R^8$ and $R^9$ may be the same or different from one another and independently mean a linear or branched alkyl group having 1 to 16 carbon atoms, $X^-$ denotes a halogen ion, and A represents a hydrogen atom or methyl group.

As specific preferable examples of the antimicrobial monomers, may be mentioned vinylbenzyl-dimethyl-n-octylammonium salts, vinylbenzyldimethyl-n-decylammonium salts, vinylbenzyldimethyl-n-dodecyl-ammonium salts and vinylbenzyldimethyl-n-hexadecyl-ammonium salts for examples of the antimicrobial monomers represented by the general formula (1).

As examples of the antimicrobial monomers represented by the general formula (2), may be mentioned vinylbenzyl-tri-n-butylphosphonium salts, vinylbenzyltri-n-octylphosphonium salts, vinylbenzyltri-n-decyl-phosphonium salts and vinylbenzyltri-n-dodecylphosphonium salts.

As examples of the antimicrobial monomers represented by the general formula (3), may be mentioned 2-acryloyloxyethyltrimethylammonium salts and 2-methacryloyloxyethyltrimethylammonium salts.

As examples of other antimicrobial monomers, may be mentioned acrylamidopropyltrimethylammonium salts, methacrylamidopropyltrimethylammonium salts, acryloyloxyalkylpyridinium salt compounds and methacryloyloxyalkylpyridinium salt compounds.

In the above-described respective compounds, a counter ion is preferably a chloride or bromide ion.

Polymers (including copolymers) obtained by polymerizing the above-described antimicrobial monomers exhibit the antimicrobial effect by the action of the quaternary ammonium salt structure or phosphonium salt structure contained therein.

When the polymer forming the antimicrobial gel is a copolymer, preference is given in that specific properties can be imparted to the resulting copolymer by selecting the kind of a copolymerizable monomer copolymerized with the antimicrobial monomer.

For example, when a monomer having a hydrophilic group is copolymerized with the antimicrobial monomer, the resulting copolymer has hydrophilicity in itself. When the polymer forming the antimicrobial gel has hydrophilicity, the antimicrobial gel comes to have hydrophilicity. As a result, it is easy to swell with water to easily achieve moderate viscosity.

No particular limitation is imposed on the copolymerizable monomer so far as it is copolymerizable with the antimicrobial monomer. However, it is preferable to use one or more of, for example, acrylamide, methacrylamide, N,N-dimethylacrylamide, N-methyl-acrylamide, N-methylmethacrylamide, N-vinyl-N-methyl-acetamide, N-isopropylacrylamide, N-(2-hydroxypropyl)-acrylamide, N-(2-hydroxypropyl)methacrylamide, N,N-dimethyl methacrylate, 2-hydroxyethyl acrylate, 2-hydroxyethyl methacrylate, hydroxypropyl methacrylate, 4-hydroxybutyl methacrylate, N-acryloyltris(hydroxy-methyl)methylamine, N-methacryloyltris(hydroxymethyl)-methylamine, vinylpyrrolidone and N-acryloylmorpholine in that the resulting copolymer becomes hydrophilic.

A crosslinkable monomer may be used as the whole or a part of the copolymerizable monomer. As the crosslinkable monomer, may preferably be used one or more of, for example, N,N'-methylenebisacrylamide, diethylene glycol diacrylate, diethylene glycol dimethacrylate, diethylene glycol divinyl ether, ethylene glycol dimethacrylate, poly(ethylene glycol)diacrylate, poly(ethylene glycol)dimethacrylate and poly(propylene glycol)dimethacrylate.

When the polymer forming the antimicrobial gel is a copolymer, the copolymer preferably contains the antimicrobial monomer component in a proportion of 1 to 50 mol %, particularly 3 to 10 mol %.

In the inorganic antimicrobial gel containing the specific inorganic antimicrobial agent, no particular limitation is imposed on the specific inorganic antimicrobial agent so far as it exhibits necessary antimicrobial activity and is substantially water-insoluble or hardly water-insoluble. As particular examples thereof, may be mentioned compounds containing silver, zinc, copper or an ion thereof. These compounds may be used either singly or in any combination thereof.

The specific inorganic antimicrobial agent is preferably be mixed and dispersed in the polymer in a state carried on a powdered base. As the base, may be used at least one of an inorganic compound and an organic compound. As the specific inorganic antimicrobial agent carried on an inorganic compound, may preferably be used an inorganic silver type antimicrobial agent with silver carried on calcium phosphate, bentonite intercalated with a metal ion or the like. As the organic compound as the base, may preferably be used a polyacrylic acid, polymethacrylic acid or the like having a carboxyl group capable of coordinate-bonding to a metal ion.

The powder forming the specific inorganic antimicrobial agent preferably has a particle diameter of 0.01 to 100 µm, particularly 0.1 to 10 µm, whereby the inorganic antimicrobial agent may be uniformly dispersed in the polymer and stably held in network structures present in the polymer, and a necessary antimicrobial action is developed.

The polymer forming the inorganic antimicrobial gel contains a hydrophilic group and is obtained by polymerizing, for example, a monomer having a hydrophilic group, whereby the polymer itself has hydrophilicity, and the inorganic antibacterial gel comes to have hydrophilicity. As a result, the inorganic antibacterial gel is easy to swell with water to easily achieve moderate viscosity.

As a monomer forming such a polymer as described above, is preferably used hydroxymethyl group-containing methacrylic acid or an ester thereof, hydroxyethyl group-containing methacrylic acid or an ester thereof, hydroxymethyl group-containing acrylic acid or an ester thereof, hydroxyethyl group-containing acrylic acid or an ester thereof, vinyl alcohol, glycerol, or an alkylene glycol such as ethylene glycol, propylene glycol, ethylene-propylene glycol or tetramethylene glycol, which imparts a hydroxyl group to the resulting polymer; N-acryloyltris(hydroxymethyl)methylamine, N-methacryloyl-tris(hydroxymethyl) methylamine, an allylamine salt, vinylamine or a vinylimidazole vinylimidazoline salt, which imparts an amino group to the resulting polymer; acrylamide, methacrylamide, N,N-dimethylacrylamide, N-methlacrylamide, N-methylmethacrylamide, N-vinyl-N-methlacetamide, N-isopropylacrylamide, N-(2-hydroxy-propyl)acrylamide, N-(2-hydroxypropyl)methacrylamide, vinylpyrrolidone or N-acryloylmorpholine, which imparts an amide group to the resulting polymer; acrylic acid, methacrylic acid, maleic anhydride or an alkali metal salt of such a carboxylic acid, N,N-dimethyl methacrylate, N,N-dimethylethyl acrylate, N,N-dimethylethyl methacrylate, 2-hydroxyethyl acrylate, 2-hydroxyethyl methacrylate, hydroxypropyl methacrylate, or 4-hydroxybutyl methacrylate, which imparts a carboxyl group to the resulting polymer; an alkali metal salt of sulfonic acid, which imparts a sulfonic group to the resulting polymer; a vinylbenzyldimethyl-n-octylammonium salt, vinylbenzyldimethyl-n-decylammonium salt, vinylbenzyldimethyl-n-dodecylammonium salt, vinylbenzyl-dimethyl-n-hexadecylammonium salt, 2-acryloyloxyethyl-trimethylammonium salt, 2-methacryloyloxyethyltrimethylammonium salt, acrylamidopropyltrimethylammonium salt, methacrylamidopropyltrimethylammonium salt, styrene ammonium salt, vinylpyridinium salt, acryloyloxyalkylpyridinium salt compound or methacryloyloxyalkylpyridinium salt compound having a chloride ion or bromide ion as a counter ion, which imparts a quaternary ammonium salt group to the resulting polymer; or an alkyleneimine or alkyleneamine, which imparts at least one of a polyether chain and a polyamine chain to the resulting polymer.

The polymer forming the inorganic antimicrobial gel may be a copolymer. In this case, at least two of the abovementioned monomers may be suitably chosen for use. In this case, preference is given in that specific properties can be imparted to the resulting copolymer.

A crosslinkable monomer may be used as the whole or a part of copolymerizable monomers forming the copolymer. As the crosslinkable monomer, may be used the same monomer as that usable in the antimicrobial gel described above.

The inorganic antimicrobial gel described above preferably contains the specific inorganic antimicrobial monomer in a proportion of 0.001 to 10.0% by mass, particularly 0.005 to 1.0% by mass, more particularly 0.01 to 0.1% by mass.

No particular limitation is imposed on the process for obtaining the polymer forming the antimicrobial gel or inorganic antimicrobial gel described above, and a polymerization process generally used, specifically, a radical polymerization reaction using a radical polymerization initiator may be utilized.

As the radical polymerization initiator, any radical polymerization initiator may be used without particular limitation so far as it is generally used. As examples thereof, may be mentioned hydrogen peroxide, ammonium persulfate, potassium persulfate, t-butyl hydroperoxide, azobisisobutyronitrile, 2,2'-azobis(2-methylpropionamide)dihydrochloride, 2,2'-azobis[2-(2-imidazolin-2-yl)propane]dihydrochloride and 2,2'-azobis(2-amidinopropane)dihydrochloride. In addition, publicly known redox initiators, for example, hydrogen peroxide and ferrous sulfate, and potassium persulfate and sodium hydrogensulfite may also be used.

As a solvent used in the polymerization reaction, may be used water, a mixed solvent of water and a water-soluble organic solvent, etc. As specific examples of the water-soluble organic solvent, may be mentioned alcohols such as methanol, ethanol, isopropanol and n-propanol, amide compounds such as formamide and dimethylformamide, and polar solvents such as dioxane, acetonitrile and dimethyl sulfoxide.

The polymerization reaction is only required to conduct the reaction at a temperature and for a period of time according to the kinds of the monomer(s) and radical polymerization initiator used and other conditions. For example, the polymerization reaction is conducted at a temperature of about 50 to 90° C. for about 3 to 24 hours. In this polymerization reaction, it is necessary to conduct the reaction under an inert gas atmosphere with, for example, nitrogen gas.

The resultant polymer permits providing antimicrobial gel, which is a jam-like fluid having suitable viscosity, by swelling it with water.

In the present invention, the antimicrobial gel preferably has a viscosity of 8.0 to 30.0 $Nsm^{-2}$, particularly 8.5 to 24.0 $Nsm^{-2}$ as measured at room temperature and a shear rate of 6.8 to 17 $sec^{-1}$.

Although the construction of the core sample collector and the method of taking a core sample according to the present invention have been described specifically above, the present invention is not limited to the above-described embodiments, and various modifications may be made in the present invention.

For example, in the core sample collector according to the present invention, no particular limitation is imposed on the kind and mode of operation thereof so far as it has a cylinder functioning as a sampling tube, which accommodates a core sample, and a piston moving in the interior of the cylinder and having the specific structure, and so the core sample collector may be, for example, an advanced piston corer (APC) having a structure that a core barrel functioning as a sampling tube is arranged within a cylindrical outer barrel provided with a drill bit at the tip thereof.

In addition, with respect to the sterilizing agent-applying mechanism, no particular limitation is imposed on the applying mechanism thereof so far as a sterilizing agent can be applied to the inner peripheral wall surface of the cylinder. For example, it may be a structure that a sterilizing agent is applied by a roller brush or the like.

Further, with respect to the scraping member, no limitation is imposed on the material and form thereof so far as the sterilizing agent applied to the inner peripheral wall surface of the cylinder can be surely scraped and removed.

According to the core sample collector of the present invention, the sterilizing agent is applied to the inner peripheral wall surface of the cylinder by the sterilizing agent-applying mechanism, and this sterilizing agent is thereafter scraped by the scraping member, whereby a sterilized or a biologically clean state is surely created.

In the method of taking a core sample according to the present invention, the sterilizing agent is applied to the inner peripheral wall surface of the cylinder immediately before the core sample comes into contact with the inner peripheral wall surface, whereby a sterilized or a biologically clean state is created, and so the objective core sample is prevented from being biologically contaminated by adhesion of adventitious nonindigeneous microorganisms.

In addition, the sterilizing agent is surely removed from the inner peripheral wall surface by the scraping member and is not brought into direct contact with the core sample, and so the resultant core sample can be provided as a core sample that surely retains its natural biological environment and is suitable for use in researches on microorganisms.

Further, by using the antimicrobial polymeric gel as the sterilizing agent, a sterilized or a biologically clean state on the inner peripheral wall surface of the cylinder can be surely created. In addition, the sterilizing agent is surely removed from the inner peripheral wall surface by the scraping member, so that the biological environment of the core sample is not disordered by contact of the sterilizing agent with the core sample.

The present invention will hereinafter be described by the following examples. However, the present invention is not limited thereby.

EXAMPLE 1

A core sample was collected from a sediment layer on the sea bottom by using a piston corer comprising a cylinder having an overall length of 5 m and an inner diameter of 8 cm and equipped with an inner tube made of polyvinyl chloride and having an overall length of 5 m in the interior thereof, and a piston equipped with a sterilizing agent-applying mechanism filled with a crosslinked polyacrylamide gel obtained by copolymerizing a quaternary ammonium salt as a sterilizing agent, and having an overall weight of 500 kg and the structure shown in FIG. 1.

After the piston corer was recovered on a ship on the sea surface, the inner tube was taken out of the interior of the cylinder and cut together with the core sample received therein along a section perpendicular to an axial direction so as to give core sample pieces each having a length of 50 cm.

In each of the sample pieces obtained in the above-described manner, only the inner tube covering the outer peripheral wall surface thereof was cut and divided along the axial direction to separate the core sample contained therein from the sample piece so as not to disorder the core sample, thereby obtaining test pieces each composed of a gutter-like inner tube piece.

A marine agar medium was stuck on the inner peripheral wall surface of the test piece that had been in a state coming into contact with the core sample in such a manner that no bubble was present between the medium and the inner peripheral surface. Thereafter, the test piece was contained in a sterilized bag and incubated at room temperature, thereby culturing microorganisms.

The number of colonies of microorganisms formed between the inner peripheral wall surface of the test piece and the medium was visually counted.

The result is shown in Tables 1 and 2.

EXAMPLE 2

A core sample was collected from a sediment layer on the sea bottom and evaluated in the same manner as in Example 1 except that a piston corer equipped with a piston provided with KIM TOWEL (trademark, product of CRECIA Corporation) impregnated with a povidone-iodine bactericide was used.

The result is shown in Tables 1 and 2.

COMPARATIVE EXAMPLE 1

The number of colonies of microorganisms on the inner peripheral wall surface of the inner tube was counted in the same manner as in Example 1 except that a piston provided with no sterilizing agent-applying mechanism for applying a sterilizing agent was used in place of the piston in Example 1.

The result is shown in Tables 1 and 2.

TABLE 1

| Depth (cm) | Example 1 Number of colonies (Count/cm$^2$) | Example 2 Number of colonies (Count/cm$^2$) | Comparative Example 1 Number of colonies (Count/cm$^2$) |
| --- | --- | --- | --- |
| 0~100 | — | — | — |
| 100~110 | 5 | 5 | 17 |
| 110~120 | 4 | 2 | 10 |
| 120~130 | 2 | 1 | 16 |
| 130~140 | 2 | 0 | 4 |
| 140~150 | 1 | 0 | 7 |
| 150~160 | 0 | 1 | 5 |
| 160~170 | 0 | 0 | 5 |
| 170~180 | 2 | 0 | 6 |
| 180~190 | 0 | 0 | 3 |
| 190~200 | 1 | 0 | 7 |
| 200~210 | 3 | 2 | 8 |
| 210~220 | 0 | 0 | 10 |
| 220~230 | 2 | 1 | 2 |
| 230~240 | 0 | 0 | 5 |
| 240~250 | 1 | 0 | 9 |

TABLE 2

| Depth (cm) | Example 1 Number of colonies (Count/cm$^2$) | Example 2 Number of colonies (Count/cm$^2$) | Comparative Example 1 Number of colonies (Count/cm$^2$) |
| --- | --- | --- | --- |
| 250~260 | 2 | 0 | 4 |
| 260~270 | 0 | 0 | 5 |
| 270~280 | 1 | 0 | 2 |
| 280~290 | 3 | 1 | 10 |
| 290~300 | 2 | 0 | 7 |

TABLE 2-continued

| Depth (cm) | Example 1 Number of colonies (Count/cm$^2$) | Example 2 Number of colonies (Count/cm$^2$) | Comparative Example 1 Number of colonies (Count/cm$^2$) |
| --- | --- | --- | --- |
| 300~310 | 0 | 0 | 7 |
| 310~320 | 0 | 0 | 4 |
| 320~330 | 0 | 0 | 10 |
| 330~340 | 0 | 0 | 9 |
| 340~350 | 0 | 0 | 4 |
| 350~360 | 0 | 0 | 3 |
| 360~370 | 0 | 0 | 8 |
| 370~380 | 0 | 0 | 4 |
| 380~390 | 0 | 0 | 1 |
| 390~400 | 1 | 0 | 2 |
| 400~410 | 2 | 2 | 3 |
| 410~420 | 0 | 0 | 2 |
| 420~430 | 0 | 0 | 5 |
| 430~440 | 1 | 0 | 1 |
| 440~450 | 0 | 0 | 11 |
| 450~460 | 0 | 0 | 4 |
| 460~470 | 1 | 0 | 2 |
| 470~480 | 0 | 1 | 3 |
| 480~490 | 0 | 1 | 1 |
| 490~500 | 0 | 0 | 1 |

In Table 1, the number of colonies was not counted from the surface layer to a depth of 100 cm because a core sample was soft and collected in an agitated state.

In Comparative Example 1, many of microorganisms frequently collected on the ground or in the sea, or so-called nonindigeneous microorganisms were identified as microorganisms forming the colonies visually observed on the inner peripheral wall surface of the inner tube.

In Examples 1 and 2 on the other hand, such nonindigeneous microorganisms as described above were scarcely identified.

It is apparent from the above results that a sterilized or a clean state on the inner peripheral wall surface of the cylinder coming into contact with the intended core sample can be achieved with high probability by collecting the core sample using the core sample collector according to the present invention, and a core sample free of contamination with nonindigeneous microorganisms can thus be provided.

What is claimed is:

1. A core sample collector comprising:
   a cylinder extending in a vertical direction,
   a piston which is movably arranged within the cylinder, and which includes a piston body,
   sterilizing agent-applying means for applying a sterilizing agent to an inner peripheral wall surface of the cylinder, and
   at least one sterilizing agent-scraping member for scraping the sterilizing agent from the inner peripheral wall surface of the cylinder after the sterilizing agent has been applied by the sterilizing agent-applying means as the piston moves within the cylinder,
   wherein the at least one sterilizing agent-scraping member comprises an upper piston ring and a lower piston ring,
   wherein the upper piston ring and lower piston ring are both arranged to project outward in a radial direction from an outer peripheral surface of the piston body and to slidably contact the inner peripheral wall surface of the cylinder, and
   wherein the sterilizing agent-applying means comprises sterilizing agent arranged in a space defined between the piston, the cylinder, the upper piston ring and the lower piston ring.

2. The core sample collector according to claim 1, wherein the sterilizing agent-applying means further comprises a sterilizing agent carrier arranged within the space formed between the piston, the cylinder, the upper piston ring and the lower piston ring, and wherein the sterilizing agent is carried and held by the sterilizing agent carrier.

3. The core sample collector according to claim 2, wherein the sterilizing agent comprises one of an antimicrobial and a bactericidal plastic polymeric substance.

4. A method of using the core sample collector of claim 3 comprising:
   contacting the cylinder against a surface from which a core sample is to be taken; and
   causing relative movement between the cylinder and the piston such that: (i) the sterilizing agent-applying means applies sterilizing agent to the inner peripheral wall surface of the cylinder, (ii) the sterilizing agent-scraping member scrapes the sterilizing agent from the inner peripheral wall, and (iii) a core is received in the cylinder.

5. A method of using the core sample collector of claim 2 comprising:
   contacting the cylinder against a surface from which a core sample is to be taken; and
   causing relative movement between the cylinder and the piston such that: (i) the sterilizing agent-applying means applies sterilizing agent to the inner peripheral wall surface of the cylinder, (ii) the sterilizing agent-scraping member scrapes the sterilizing agent from the inner peripheral wall, and (iii) a core is received in the cylinder.

6. The core sample collector according to claim 1, wherein the sterilizing agent comprises one of an antimicrobial and a bactericidal plastic polymeric substance.

7. A method of using the core sample collector of claim 6 comprising:
   contacting the cylinder against a surface from which a core sample is to be taken; and
   causing relative movement between the cylinder and the piston such that: (i) the sterilizing agent-applying means applies sterilizing agent to the inner peripheral wall surface of the cylinder, (ii) the sterilizing agent-scraping member scrapes the sterilizing agent from the inner peripheral wall, and (iii) a core is received in the cylinder.

8. A method of using the core sample collector of claim 1 comprising:
   contacting the cylinder against a surface from which a core sample is to be taken; and
   causing relative movement between the cylinder and the piston such that: (i) the sterilizing agent-applying means applies sterilizing agent to the inner peripheral wall surface of the cylinder, (ii) the sterilizing agent-scraping member scrapes the sterilizing agent from the inner peripheral wall, and (iii) a core is received in the cylinder.

9. The core sample collector according to claim 1, wherein the upper piston ring is arranged on the outer peripheral surface of the piston body.

10. The core sample collector according to claim 1, wherein the lower piston ring is arranged on the outer peripheral surface of the piston body.

11. The core sample collector according to claim 1, wherein the upper piston ring and the lower piston ring are both arranged on the outer peripheral surface of the piston body.

12. The core sample collector according to claim 1, further comprising an additional upper piston ring arranged substantially parallel to the upper piston ring and on an upper portion of the outer peripheral surface of the piston body.

13. The core sample collector according to claim 1, further comprising an additional lower piston ring arranged substantially parallel to the lower piston ring and on a lower portion of the outer peripheral surface of the piston body.

14. The core sample collector according to claim 13, further comprising an additional upper piston ring arranged substantially parallel to the upper piston ring and on an upper portion of the outer peripheral surface of the piston body.

15. The core sample collector according to claim 1, wherein the upper piston ring and the lower piston ring are arranged substantially parallel to each other and separated from each other.

16. The core sample collector according to claim 1, wherein the piston body comprises a recessed portion between the upper piston ring and the lower piston ring, and the recessed portion has an outer diameter that is smaller than a diameter of the piston body.

17. The core sample collector according to claim 1, wherein the upper piston ring and the lower piston ring are O-rings.

18. The core sample collector according to claim 17, wherein the O-rings are arranged on and around the outer peripheral surface of the piston body.

* * * * *